United States Patent [19]
Zorn

[11] Patent Number: 5,469,743
[45] Date of Patent: Nov. 28, 1995

[54] DYNAMIC SURFACE WAVE ROLL INSPECTION DEVICE

[76] Inventor: Roger H. Zorn, 84 Crescent Blvd. Ext., Coraopolis, Pa. 15108

[21] Appl. No.: 82,043

[22] Filed: Jun. 24, 1993

[51] Int. Cl.⁶ .................................................. G01N 29/04
[52] U.S. Cl. ............................................ 73/627; 73/620
[58] Field of Search .......................... 73/584, 598, 600, 73/620, 622, 627

[56] References Cited

U.S. PATENT DOCUMENTS

| | | | |
|---|---|---|---|
| 3,602,036 | 8/1971 | Peterson | 73/67.8 |
| 4,624,289 | 12/1986 | Fukuda et al. | 73/622 |
| 4,641,531 | 2/1987 | Reeves et al. | 73/622 |
| 4,658,649 | 4/1987 | Brook | 73/598 |
| 4,898,034 | 2/1990 | Kupperman et al. | 73/644 |

OTHER PUBLICATIONS

N. C. Nelson et al, "Surface Wave Ultrasonic Inspection for the Detection and Removal of Cracks in Indefinite Chill Double Poured HSM Work Rolls", AIME Conference Montreal, Oct. 1992, 9 pages.

*Primary Examiner*—Richard Chilcot
*Assistant Examiner*—Max H. Noori
*Attorney, Agent, or Firm*—Patrick J. Viccaro

[57] ABSTRACT

A method and apparatus is provided for dynamically inspecting rolling mill rolls to locate surface defects in the rolls by applying an ultrasonic shear wave circumferentially to a rotating roll, wiping liquid from the surface to remove surface contaminants, and sensing reflections representative of any roll surface defects.

9 Claims, 3 Drawing Sheets

DYNAMIC SURFACE WAVE ROLL INSPECTION DEVICE

FIELD OF INVENTION

This invention relates to a method and apparatus for nondestructive testing of rolling mill rolls for detecting surface defects. More particularly, the invention relates to dynamic inspection of such rolls using ultrasonic waves.

BACKGROUND

For many years it has been common practice to utilize ultrasonic surface waves to inspect the surfaces of forged and cast steel rolling mill work rolls for the presence of defects such as firecracks and spalling. Such defects occur as a result of normal wear and tear through routine usage in the hot strip mill. Typically, an ultrasonic beam is introduced into the surface of the roll at the critical angle of approximately 58 degrees or greater, which results in the generation of surface waves which generally travel circumferentially along the surface of the roll. The waves are highly influenced by the presence of very small defects, cracks, and pores, as well as dirt, grease, and water on the roll surface. These conditions cause a portion of the surface wave to be reflected back, and received by an ultrasonic wave transducer which generates the wave. This is known as the pulse-echo ultrasonic inspection technique. Such known practices are disclosed in a paper by N. C. Nelson and C. O. Zamuner, entitled "Surface Wave Ultrasonic Inspection For The Detection and Removal of Cracks in Indefinite Chill Double Poured HSN Work Rolls" proceedings of AIME Mechanical Working and Processing Conference, Montreal, October 1992.

In common practice, the method of performing this type of test is strictly manual. First, the work roll must be in a finished or semi-finished ground state such as by roll grinding. The roll is then set down on chalks or neck supports so that access can be made to the entire roll body. An important and necessary step is to wipe and dry the ground roll to remove all surface contaminants before inspect in.

A bead of ordinary oil or ultrasonic couplant is then applied along the top of the roll from end to end on the roll body. The manually held surface wave transducer is placed in contact with the stationary roll on the area of oil and oriented to propagate the wave circumferentially around the roll body. The transducer is then moved across the body of the roll.

The ultrasonic instrument sensitivity and range may be adjusted so that the interference echo at 180 degrees roll circumference is seen at 80 to 100% of full screen on the instrument base line and at an amplitude of 100%. Any defect indications would be seen between the initial pulse and the interference echo. Typically these will appear as echoes on a cathode ray tube (CRT) display. This gives only a general indication of the location and type of defect on the roll surface. In order to locate the indicated defect, a manual step must be performed.

It is customary to locate the actual area where the echoes are generated by moving an oil covered finger in the path of the sound beam until the echo from the finger is coincident with the echo from the surface of the roll. If the echo remains after wiping off the suspect area with the finger and a rag then it is most likely a fire crack in the roll surface. If the echo disappears, then the indicated defect was only debris or contaminate on the roll surface.

After half of the roll has been inspected by this tedious technique, the roll is again cleaned and a new bead of oil applied. The transducer is manually reversed to circumferentially inspect the other 180 degrees of the roll surface and the above roll is rotated 90 degrees after both halves have been inspected, wiped down again and the whole process repeated. This last step is to insure that there are no uninspected areas on the roll, specifically, interference echo at 180 degrees.

After such inspection, if crack remnants have been found, the work roll must be loaded back into the roll grinder, usually resulting in more wasted time in waiting for the crane operator and the time to manhandle the roll back into the grinder. The roll must then be ground again to remove the surface damage, and then reinspected. This results in loss of time and productivity, and the added expense of the grinding operations.

What is needed is a method and apparatus for improving the efficiency of inspecting work rolls by reducing the time for inspections and for minimizing costly time spent on the grinding equipment. The method and apparatus should be done dynamically on a rotating work roll instead of stationary rolls and should minimize false echoes created by contaminants and debris on the roll surface. The invention should be useful in conjunction with the roll grinding equipment in order to minimize roll handling operations.

SUMMARY OF THE INVENTION

In accordance with the present invention, a method and apparatus is provided for dynamically inspecting rolling mills rolls for surface defects. The apparatus includes a housing having an arcuate surface to fit the contour of a roll surface, an ultrasonic angle beam transducer positioned in the housing to generate an ultrasonic shear wave in the roll surface, a means for wiping the roll surface and a means for sensing a reflection from defects in the roll surface. The method includes rotating the rolling mill roll about its longitudinal axis, wiping liquid from the roll surface, and generating the ultrasonic shear wave in the roll surface substantially circumferentially in the direction of rotation, and sensing any reflection indicating the surface defects.

DESCRIPTION OF THE INVENTION

Figure 1:
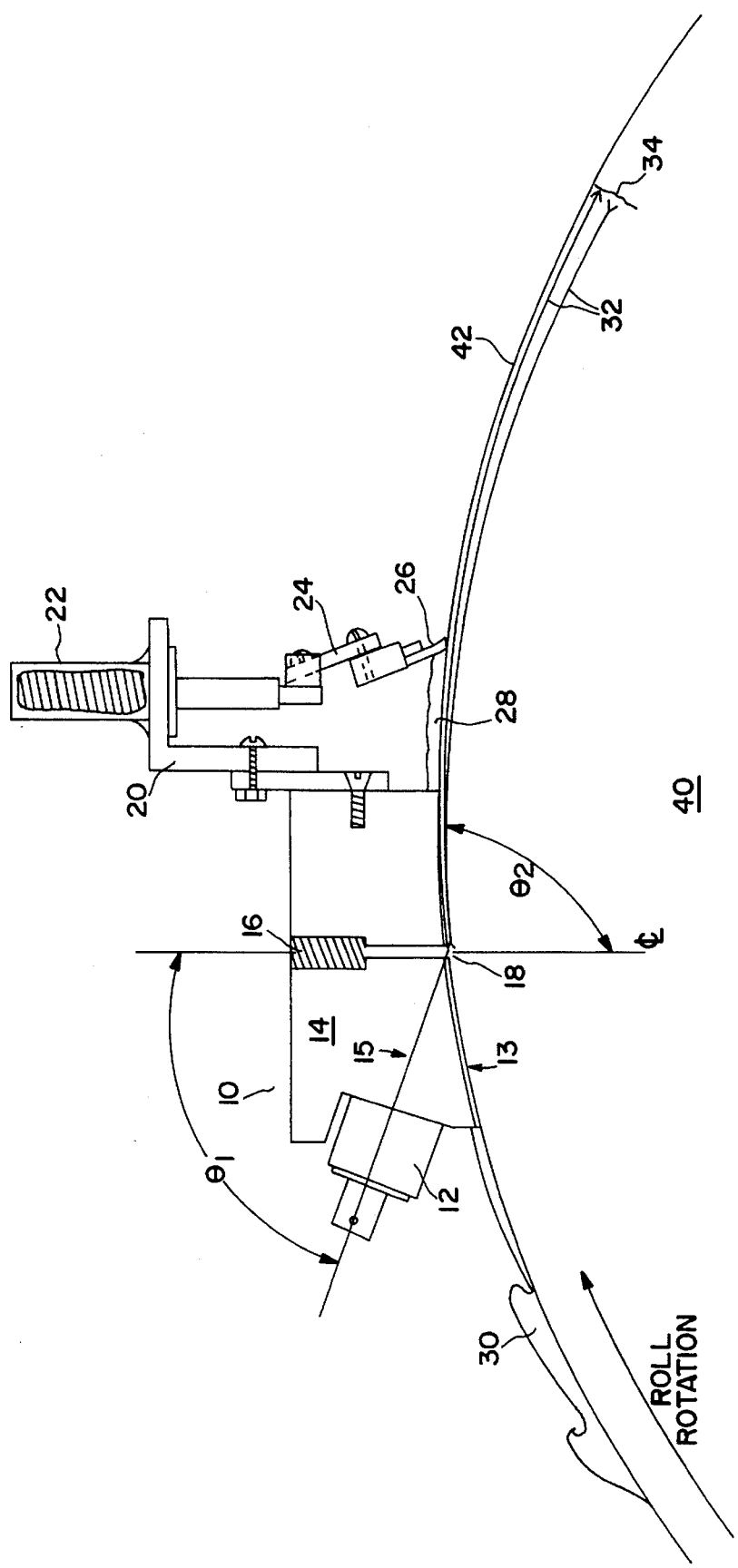
FIG. 1 is a side elevation view of the apparatus of the present invention adjacent to roll surface.
Figure 3:
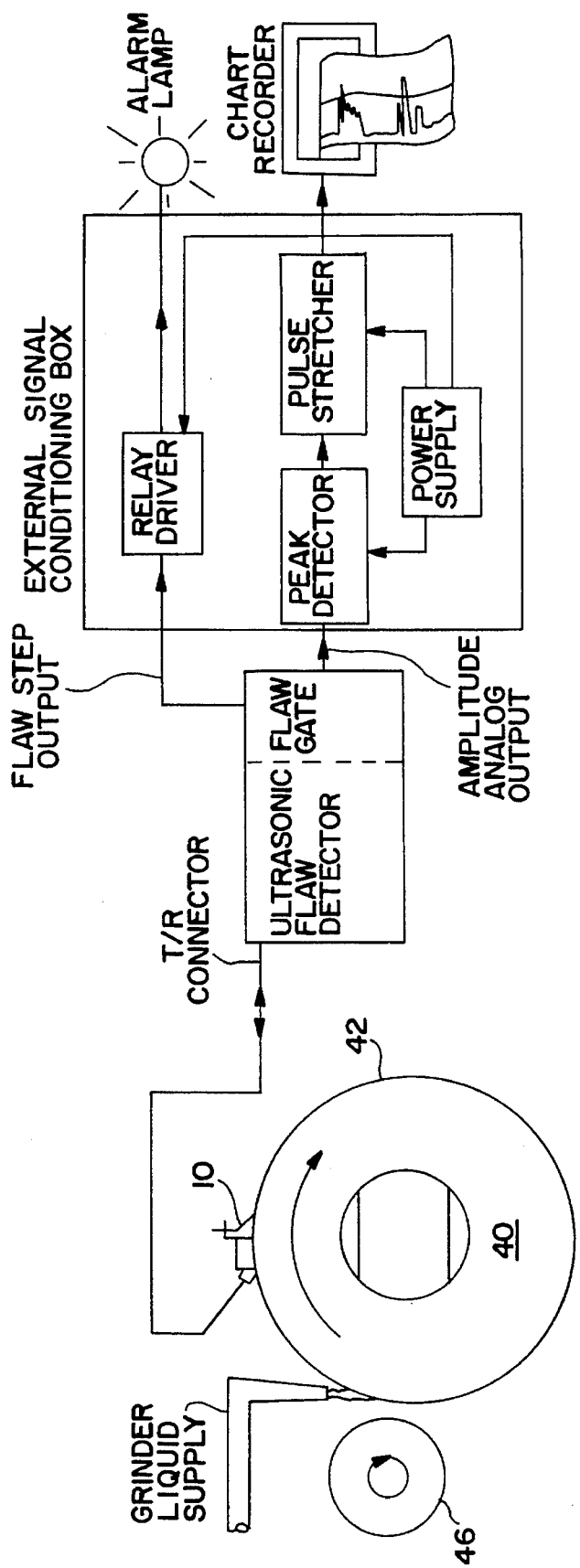
FIG. 3 is a schematic diagram of the electrical circuit of the present invention.

As shown in FIG. 1, the roll inspection device 10 of the present invention includes an ultrasonic angle beam transducer 12 positioned within housing 14 adjacent the surface 42 of rolling mill roll 40. Housing 14 includes an arcuate bottom surface 13 contoured to fit in close tolerance to roll surface 42. Attached to housing 14, such as by brackets 20, is a means 24 for wiping liquid from the surface 42 of roll 40. A means for displaying or recording a sensed reflection is shown in FIG. 3.

The transducer 12 must generate an ultrasonic longitudinal wave capable of operating in the range of up to but not limited to 5 megahertz (mHZ), preferably in the range of 1 to 5 mHZ for narrow to broad band capability. A suitable transducer is manufactured by Panametrics, Inc., Model No. A-403S, operating at 2.25 mHZ.

As shown in FIG. 1, the transducer is oriented within the housing to direct the longitudinal ultrasonic beam at an incident angle $\phi_1$, to generate a surface shear wave in the surface of the roll body. The refracted angle of the surface wave is measured from the center line of the roll to the tangent line as $\phi_2$. In theory, the incident angle of 58.7 degrees is the critical angle for generation of surface waves. Reference the handbook titled *Refracted Angle Tables, Vol. 1.* published by Automation industries, Inc. formerly of Danbury, Connecticut, pp. 30, 31, and 32.

In a prototype of the present invention, the incident angle of the housing 14 is 65 degrees, utilizing standard surface wave housing supplied to by a manufacturing source. This angle of incidence is greater than the 58.7 degrees stated in the refracted angle handbook, and perform quite adequately in the generation of surface waves for the detection of firecracking in the surface of rolls and cylindrical shapes.

Housing 14 is contoured to achieve optimum coupling efficiency of the ultrasonic beam 15 into roll surface 42. As known, liquid on the surface of the roll aids in achieving ultrasonic coupling. By the present invention, liquid on roll surface 42 is used to achieve the coupling. In a preferred embodiment, housing 14 includes one or more inlet ports 16 for injecting fluid as a couplant to surface 42. The fluid such as oil or water may be used instead of or in addition to any fluid that may already be on the roll surface.

Housing 14 my be made of a material which will not adversely affect the ultrasonic wave. A material such as acrylic is preferred. Housing 14 is made of a clear acrylic plastic, such as Lucite brand, made by Dupont Corporation.

Attached to the front of housing 14, downstream of the ultrasonic wave is a means 24 for wiping fluid from surface 42 of roll 40. Means 24 may be mounted to housing 14 in any of various ways which are not critical to the present invention. As shown in FIG. 1, means 24 includes a wiper 26 for contacting surface 42 for removing liquid and debris from the surface wiper 26 is mounted through brackets 20 to a spring biasing means 22 for facilitating the desirable pressure of wiper 26 against surface Wiper 26 may be made of a soft, pliable, resistant material, such as rubber, to provide effective wiping or squeegee action. It has been found that the wiper 26 should be wider than the width of housing 14 to facilitate a wide, clean, relatively dry surface.

Figure 2:
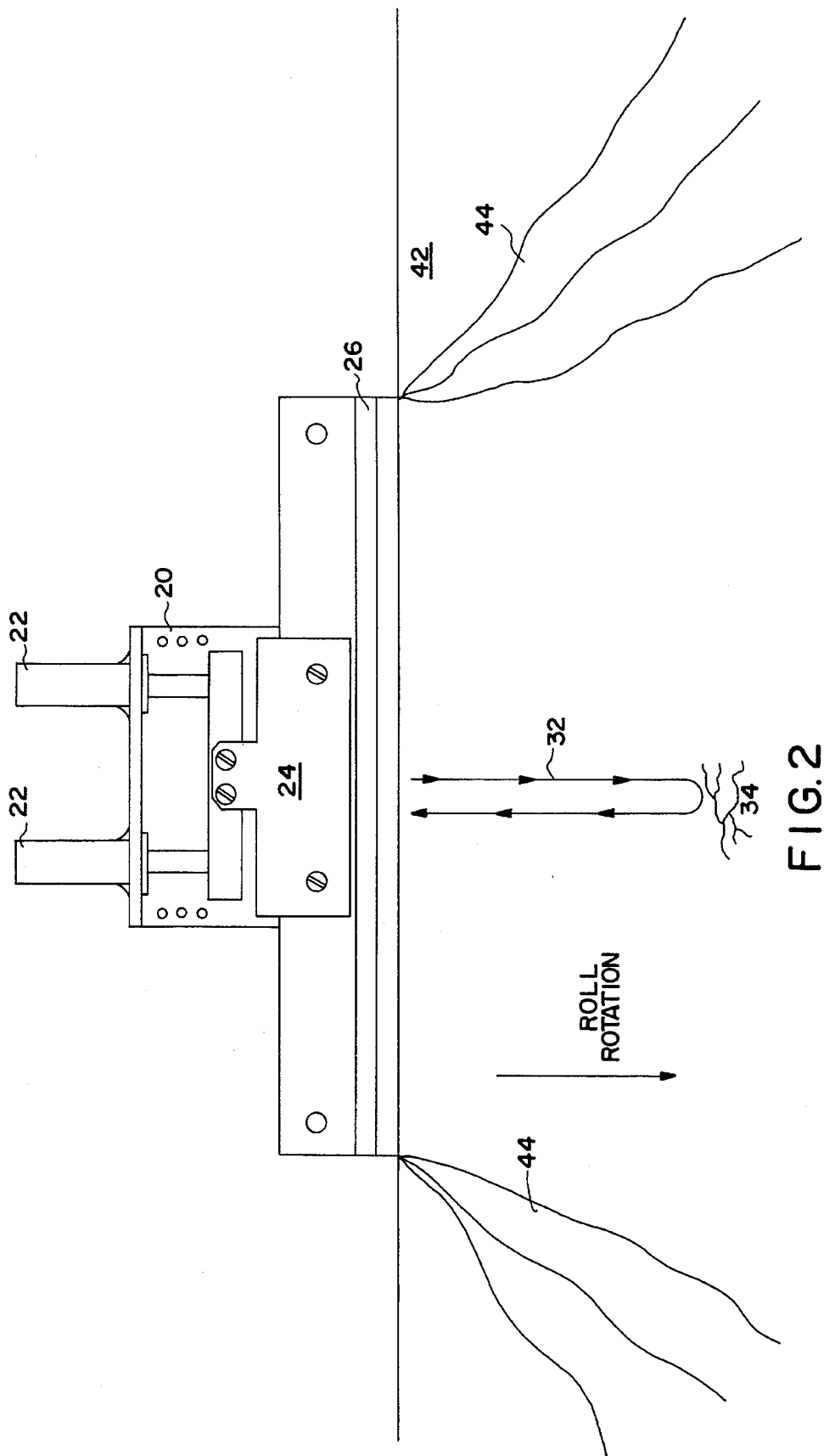
FIG. 2 is a front elevation view of the apparatus of the present invention.

As shown in FIG. 2, housing 14 (not shown) has attached to its front a plurality of spring means 22 for controlling the pressure exerted to wiping means 24 and wiper blade 26 against roll surface 42.

FIG. 3 is a schematic diagram of the present invention showing the circuitry suitable for propagating, receiving, conditioning, displaying and recording the ultrasonic signals. The circuit shows the roll inspection device 10 which is comprised of the contoured wedge, ultrasonic angle beam transducer and spring biased wiping mechanism. The device 10 is held in place with a flexible dial gage base arm (not shown) for locking into position and for swinging out of position when not in use. With the grinding water turned on, the roll is rotated between 10 and 40 R. P. M. with an overlapping traverse. The transducer assembly 10 is connected to an ultrasonic flaw detector which transmits the pulse and receives echoes relating to surface flaws from the transducer assembly. The received echoes are amplified, converted into video signals, and then processed by the flaw gate. The flaw step output drives an alarm lamp when the defect exceeds a predetermined threshold. The amplitude analog output of the flaw gate is processed by the peak detector and pulse stretcher to detect and hold the peak value of the defect signal for a pre-determined time to facilitate the recording on a chart recorder.

In the operation of the present invention, the work roll to be inspected would be placed in an apparatus for rotating the roll about its longitudinal axis. Preferable, the roll would be inserted into a roll grinder for rotation without the grinding wheel 46 being in contact. The grinder liquid 30 may be used alone or in combination with additional fluid injected through inlet ports 16 to couple the ultrasonic wave to the roll surface 42. As the 40 roll rotates, the inspect ion device would be placed in contact with the rotating roll. Wiper means 24 wipes and cleans surface 42 of liquid and debris trapped in area 28 behind 26 and housing 14.

As shown in FIG. 2, the surface 42 in front of wiper 26 is clean and relatively dry while the collected or trapped fluid will be directed aside as illustrated by reference numerals 44.

Although there is no intent to be bound by theory, it is believed that the ultrasonic wave 15 generated by transducer 12 escapes from housing 14 at location 18 and enters roll surface 42. The liquid facilitates coupling of the wave to the surface as the liquid is sloughed up under the housing 14 by rotation of the roll 40 and/or by injection. The electronic flaw gate of the pulse echo ultrasonic instrument is set ahead to the wiped clean, relatively dry surface of the roll. The wave travels forward circumferentially in the direction of roll rotation from location 18 to wiper 26. Although the wiper diverts the coupling fluid to each side of the wiper, the ultrasonic wave passes under the wiper 26 with negligible loss of signal. An interface signal corresponding to the wiper location my be displayed. After passing under wiper 26, the surface wave 32 propagates in the clean relatively dry surface. Wave 32 is sensitive to any defects 32 in surface 42. Defects 32 would be caused by flaws, firecracks, pores in the surface and not by debris or contaminants on the roll surface.

In the operation and set up of the present invention, the flaw gate of the pulse-echo ultrasonic device is positioned in start and width to provide a window in the clean and dry surface. The echo indications my be captured as to the number of flaws and amplitude and recorded on a strip chart recorder. The data may be displayed in known ways from the analog output of the flaw amplitude. Additional equipment may be connected through electronic or electrical circuitry to display the data on CRTs, hard copy form.

Without departing from the scope of the present invention, it should be understood that present invention my include a single transducer and a single-channel, however multiple transducers my be mounted side by side to provide a wider scanning path on the roll surface. Furthermore, ultrasonic transducers my be driven by known ultrasonic multiplexers to generate and receive ultrasonic signals from each transducer in sequential ring counter fashion to relatively high speeds. In order to optimize detection of irregularly oriented surface defects 34, the ultrasonic transducers my be oriented so that the sound waves have both a circumferential and a helical component in the roll surface. A wedge with several angles of transducer orientation may be built so that the sound wave travels not only circumferentially, but in a helix around the roll body to optimize detection of irregularly oriented cracks; i.e.: cracks that are not silly running in a longitudinal direction along the roll body. This would fall under the category of a multiplexed system, which is within the scope of the present invention.

What is claimed is:

1. An apparatus for dynamically inspecting rolling mill rolls for surface defects by rotating the rolls and by using ultrasonic waves, the apparatus comprising:

a housing having an arcuate bottom surface adapted to the contour of a roll surface to be inspected when placed adjacent the roll surface;

an ultrasonic angle beam transducer positioned within the housing to generate an ultrasonic shear wave substantially circumferentially in the roll surface;

means for wiping the roll surface downstream of the wave generator for cleaning liquid from the roll surface, said liquid being present to facilitate transmission of the ultrasonic wave into the roll surface; and means for sensing a pulse echo reflection from within the wiped roll surface upon detection of a roll surface defect.

2. An apparatus of claim 1, wherein the apparatus, includes a means for injecting fluid through the housing and onto the roll surface in the vicinity that the ultrasonic wave enters the roll surface.

3. An apparatus of claim 1, wherein the wiping means includes a spring biasing means for pressuring the wiping means against the roll surface.

4. An apparatus of claim 1, wherein two or more ultrasonic transducers are positioned within the housing substantially side-by-side to provide wider inspection area.

5. An apparatus of claim 1, wherein the generator is oriented to provide a helical component in the roll surface.

6. A method for dynamically inspecting rolling mill rolls for locating surface defects using ultrasonic waves, the method comprising:

rotating a roll to be inspected about its longitudinal axis;

providing a liquid on the roll surface;

wiping the liquid to provide a relatively clean dry surface;

generating an ultrasonic shear wave generally circumferentially in the roll surface for detecting surface flaws in the clean dry roll surface; and sensing a pulse echo reflection from the roll surface upon detection of a roll surface defect.

7. The method of claim 6 further including injecting a liquid onto the roll surface in the vicinity where the ultrasonic wave enters the roll surface.

8. The method of claim 6, wherein generating ultrasonic waves includes a plurality of waves side-by-side.

9. The method of claim 6, wherein generating the wave includes generating a helical component.

* * * * *